006
United States Patent [19]

Huang et al.

[11] Patent Number: 4,927,571

[45] Date of Patent: May 22, 1990

[54] PREPARATION OF INJECTABLE DOXORUBICIN/LIPOSOME SUSPENSION

[75] Inventors: Anthony H. Huang, Sunnyvale; Satya Krishnan, Mountain View, both of Calif.

[73] Assignee: Liposome Technology, Inc., Menlo Park, Calif.

[21] Appl. No.: 51,418

[22] Filed: May 18, 1987

[51] Int. Cl.$^5$ ............... A61K 37/22; A61K 45/05; B01J 13/02
[52] U.S. Cl. ............... 264/4.3; 424/450; 428/402.2; 436/829; 514/893; 514/894; 514/908
[58] Field of Search ............... 264/4.3; 428/402.2; 424/450; 436/829; 514/893, 894, 908

[56] References Cited

U.S. PATENT DOCUMENTS

| | | | |
|---|---|---|---|
| 4,460,577 | 7/1984 | Moro et al. | 424/450 |
| 4,515,736 | 5/1985 | Deamer | 264/4.3 |
| 4,544,545 | 10/1985 | Ryan et al. | 424/450 X |
| 4,687,762 | 8/1987 | Fukushima et al. | 514/34 |
| 4,797,285 | 1/1989 | Barenholz et al. | 424/450 |

FOREIGN PATENT DOCUMENTS

WO86/01102  2/1986  PCT Int'l Appl. ............... 424/450

*Primary Examiner*—Richard D. Lovering
*Attorney, Agent, or Firm*—Peter J. Dehlinger

[57] ABSTRACT

An doxorubicin/lyposome composition which can be reconstituted from a lyophilized form to an injectable liposome suspension having selected liposome sizes in the size range between 0.1 and 0.5 microns, and between about 85–95% liposome-entrapped doxorubicin. The composition is prepared by reconstituting a lyophilized doxorubicin/liposome composition to a liposome concentrate, then diluting the concentrate for perenteral.

6 Claims, No Drawings

PREPARATION OF INJECTABLE DOXORUBICIN/LIPOSOME SUSPENSION

1. FIELD OF THE INVENTION

The present invention relates to a novel liposome/doxorubin composition and method, and in particular, to a composition which can be stored for extended periods in lyophilized form, and reconstituted to an injectable suspension having selected liposomes sizes and between 85-95 percent liposome-entrapped doxorubicin.

2. REFERENCES

Aubel-Sadron, G., et al, Biochemie, 66:333 (1984).
Forssen, E.A., et al, Proc Nat Acad Sci, USA( 78(3) 1873 (1981)
Gabizon, A., et al, Cancer Res, 42:4734 (1982)
Gabizon, A., et al, Cancer Res, 43:4730 (1983).
Goormaghtigh, E., et al, Biochem Biophys Acta, 779:271 (1984).
Gutteridge, J.M.C. Biochem Pharm, 33(11):1725 (1984a).
Juliano, R.L., et al, Biochem Pharmacol, 27:21 (1978).
Poznansky, M.L., et al, Pharm Revs 36(4):277 (1984).
Sunamoto, J., et al, Biochem Biophys Acta, 833:144 (1985).
Szoka, F., et al, Proc Nat Acad Sci (USA) 75:4194 (1978).
Szoka, F., et al, Ann Rev Biophys Bioeng, 9:467 (1980).
Young, R.C., et al, N Eng J Med, 305:139 (1981).

3. BACKGROUND OF THE INVENTION

Doxorubicin (DXR) is a potent chemotherapeutic agent effective against a broad spectrum of neoplasms (Aubel-Sadron et al and Young}. However, clinical use of the drug in free form is limited by serious side effects and acute toxicity including malaise, nausea, vomiting myelosuppression, and severe alopecia. In addition, cumulative and irreversible cardiac damage occurs with repeated administration, which seriously limits the use of the drug in protracted treatment (Young).

One approach which has been used to reduce DXR toxicity in vivo is to administer the drug in liposome-entrapped form. Animal studies and, more recently, clinical testing demonstrate that DXR in liposome-bound form retains its therapeutic effectiveness against animal tumors, but is significantly less toxic, as judged by reduced mortality and reduction in cardiotixic effects (Forssen, Gabizon 1985). The drug-protective effect of liposomes is due, at least in part, to a marked alteration in tissue disposition and drug-release rate of the injected drug (Gabizon 1982; Gabizon 1983; Juliano).

Recent animal model studies point to three factors which are important in achieving increased therapeutic action and reduced toxicity in DXR/liposomes. One of these is liposome size. Studies aimed at determining the biodistribution and drug clearance of DXR/liposomes after intravenous administration, as a function of liposome size, have been conducted (Gabizon 1982, 1983, and U.S. Pat. application for "Liposome/Anthraquinone Drug Composition and Method, Ser. No. 806,084, filed Dec. 6, 1985, now U.S. Pat. No. 4,797,285). Briefly summarizing the results, DXR/liposomes having average sizes of between about 0.1-0.2 show increased drug levels in the liver and spleen, and decreased drug levels in heart, lung, intestine, kidney, and skeletal muscles when compared with the free drug. Liposomes of this size are thus particularly advantageous in treating liver- and spleen-localized tumors and in reducing toxicity related to drug levels in non-target tissues, particularly the heart. Liposomes in this size range also show slower drug clearance in liver and spleen tissue. The biodistribution and drug clearance rates in small unilamellar vesicles (0.03-0.08 size range approximately) was intermediate that of the larger liposomes and free drug.

For a variety of reasons, the optimal upper size limit of the liposomes is about 0.5 microns and, preferably, about 0.2-0.3 microns. First, desired target tissue regions, such as liver sinusoids and parenchyma, spleen, and bone marrow are more accessible to liposomes smaller than about 0.2-0.3 microns. Secondly, liposomes in the 0.2-0.3 micron size range can be readily sterilized by filtration through a depth filter. Vesicles of this size also show little tendency to aggregate on storage, thus reducing a potentially serious problem when the composition is administered parenterally. Finally, liposomes which have been sized down to the submicron range show more uniform biodistribution and drug clearance characteristics, since they have more uniform sizes.

A second feature of DXR/liposomes which is important to therapeutic effectiveness is the extent of chemical degradation of lipid and drug components which can occur on storage. Phospholipid degradation can take the form of hydrolytic release of fatty acyl chain groups and lipid peroxidative damage, particularly at unsaturated bond regions in lipid acyl chain moieties (Gutterage, 1984; Sunamoto). In addition, anthaquinone-type drugs, such as DXR, are themselves capable of initiating oxidative reactions (Goormaghtigh, 1984; Gutteridge, 1984a), and in the presence of lipids, appear to contribute to free radical/oxidative reactions, and also undergo rapid chemical changes on storage in liposomes, as reported in the above-cited patent application for "Liposome/Anthraquinone Drug Composition and Method".

In studies carried out in support of the just-cited application, it was found that the combined presence of a lipid-soluble free radical quencher, such as alpha-tocopheral, and a water-soluble trihydroxamic chelating agent, such as desferal, reduced peroxidative damage to lipid and drug components substantially more than the sum of individual protection provided by either protective agent alone. A key feature of this protective effect appears to involve chelation of ferric iron in a form which does not readily catalyze peroxidation formation, combined with lipid-phase free-radical quenching by the lipophilic quencher.

The toxicity of DXR/liposome formulations is also sensitive to the percentage of free drug in the formulation. Clinical trial evaluations indicate that DXR/liposomes containing moderate levels of free drug (about 35%) produce substantially greater toxicity at a 50mg/$m^2$ dose than do DXR/liposomes with low free drug (10-15%) administered at a 70 mg/$m^2$ dose. There are a variety of methods available for removing free DXR from DXR/liposomes preparations, including centrifugation, diafiltration, filtration by molecular sieve chromatography, and, as disclosed in U.S. Pat. No. 4,460,577, by filtration through an ion-exchange resin. These methods are effective in reducing free drug levels in freshly prepared DXR/liposome preparations to 10% or less of total DXR. However, on storage in solution, free drug may be gradually released as increased lipid and drug oxidative damage occurs. Conventional lyophilization/and reconstitution methods for storing DXR/liposomes in a dried state lead to substantial release of free drug on reconstitution. Conventional lyophilization and reconstitution procedures result in a substantial release of liposome-associated DXR, typically resulting in 20–30% free drug in the reconstituted liposome suspension.

4. SUMMARY OF THE INVENTION

It is therefore one general object of the present invention to provide a DXR/liposome formulation which has selected liposome size characteristics, is stable on long-term storage, and contains at least about 85%–95% DXR in liposome-associated form.

A related object of the invention is to provide a lyophilized liposome composition and liposome concentrate used in preparing such formulation.

Yet another object of the invention is to provide a method for preparing DXR/liposomes which, after long-term storage, have preselected sizes, relatively little free DXR, and minimal oxidative damage.

The invention includes, in one aspect a lyophilized doxorubicin/liposome composition which, upon reconstitution with a predetermined volume of aqueous medium, yields a liposome concentrate characterized by:
 a. a concentration of liposomes of greater than about 100 mM liposome lipid,
 b. liposome sizes predominantly in a selected size range between about 0.1 to 0.5 microns,
 c. liposome-entrapped DXR, at a concentration between about 2–10 mole percent liposome lipids, and between about 85%–95% of total DXR; and
 (d) between about 1% to 10% cryoprotectant.

In one preferred embodiment the composition is reconstituted with low-osmolarity medium or distilled water to yield a concentrate which is near physiological osmolarity. A preferred cryoprotectant is trehalose or lactose, at a concentration of about 5%.

In another aspect, the invention includes the DXR/liposome concentrate formed by reconstituting the above composition. The concentrate preferably has a physiological osmolarity, and may be further formulated to contain a lipophilic free-radical quencher and a water-soluble iron-specific chelator, to minimize free radical and oxidative damage which can occur during initial liposome preparation and storage and after reconstitution.

The invention further includes a method for preparing DXR/liposomes intended for intravenous administration in cancer chemotherapy, and having between 85%–95% DXR in liposome associated form. The method involves first, preparing a liposome dispersion characterized by:
 a. liposome sizes predominantly in a selected size range between about 0.1 to 0.5 microns,
 b. liposome-entrapped DXR, at a concentration between about 2–10 mole percent liposome lipids, and greater than about 90% liposome-associated DXR; and
 c. between about 1%–10% cryoprotectant.

The dispersion, which is preferably prepared to a lipid concentration of greater than 100 mM at physiologic osmolarity, is lyophilized for storage, then reconstituted by addition of aqueous medium, and preferably distilled water, to a reconstituted concentrate having a lipid concentration of at least about 100 mM. The percentage of free drug in the concentrate is typically about 5% higher than that in the original dispersion. The reconstituted DXR/liposomes are diluted with an injection medium, such as physiological saline, to form a liposome suspension suitable for IV injection. The percentage of free DXR in the diluted suspension is substantially the same as that in the reconstituted material.

These and other objects and features of the invention will become more fully apparent from the following detailed description of the invention.

DETAILED DESCRIPTION OF THE INVENTION

I. DXR/Liposome Preparation

The DXR/liposome concentrate and suspension of the invention is prepared from a concentrated, pre-lyophilized liposome dispersion whose preparation is described in this section. Although the suspension can be prepared by a variety of procedures, two methods :;ill be emphasized. These are (1) thin-film hydration, with subsequent sizing and treatment to remove free drug and to concentrate the suspension; and (2) solvent injection, according to a novel procedure which produces high-concentration dispersions.

A. Liposome Dispersion Components

The DXR/liposomes of the dispersion are formed from standard vesicle-forming lipids, which generally include neutral phospholipids, such as phosphatidylcholine (PC); negatively charged phospholipids, such as phosphatidylglycerol (PG), phosphatidylserine (PS), phosphatidylinositol (PI) and phosphatidic acid (PA); negatively charged sterols; such as cholesterol sulfate and cholesterol hemisuccinate; and sterols such as cholesterol. The selection of lipids is guided by considerations of (a) drug-release rate in serum, (b) drug-entrapment efficiency, (c) liposome toxicity, and (d) biodistribution and targeting properties. The effect of phospholipid and cholesterol components on in vivo drug-release rates, drug entrapment efficiency, and liposome toxicity have been examined in studies carried out in support of the above patent application for "Liposome-/Anthraquinone Drug Composition and Method". Briefly summarizing the results of those studies:

1. Negatively charged phospholipids, such as PG, PS, and PI, tend to enhance drug liposome stability, as measured by DXR release into 50% plasma. Optimal concentrations are between about 10 to 30 mole percent negatively charged lipid;

2. Cholesterol, at a concentration between about 20 to 50 mole percent, produces a 2-3 fold enhancement in DXR retention in PC liposomes, as measured by DXR release into serum, but has less stabilizing effect where negatively charged phospholipids are also present;

3. Negatively charged phospholipids appear to increase drug entrapment efficiency, although cholesterol has little effect;

4. Liposomes composed predominantly of phospholipids with saturated acyl chain moieties are more toxic than liposomes composed of corresponding unsaturated acyl chain components, although saturated lipids are less susceptible to oxidative damage and corresponding increase in toxicity on storage.

The interaction between lipid and DXR components in liposomes, and the effects of protective agents which inhibit free radical and lipid peroxidation reactions in DXR/liposomes have also been extensively studied, as reported in the above-cited patent application. The studies showed that DXR accelerates oxidative reactions in liposomes and is itself degraded by free-radical peroxidation reactions. According to an important finding of the studies, the presence of both a lipid-soluble free-radical quencher, such as alpha-tocopherol, and a water-soluble ferric iron chelator, such as desferal, produced a significantly greater inhibition of oxidative damage to lipids and drug components than would be expected from the inhibition produced by each component alone. These results suggest that inhibition of free-radical and/or peroxidative events in both the aqueous and lipophilic phases of the dispersion is crucial to achieving effective inhibition of oxidative damage in DXR/liposomes.

The lipophilic free radical scavenger used in the composition of the invention is preferably alpha-tocopherol, or a pharmacologically acceptable analog or ester thereof, such as alpha-tocopherol succinate. Other suitable free radical scavengers include butylated hydroxytoluene (BHT), propyl gallate, and their pharmacologically acceptable salts and analogs. The free radical quencher is typically included in the lipid components used in preparing the liposomes, according to conventional procedures. Preferred concentrations of the protective compound are between about 0.2 and 2 mole percent of the total lipid components making up the liposomes.

The water soluble protective agent is an iron-specific chelating agent selected from the class of natural and synthetic trihydroxamic acids and characterized by a very high binding constant for ferric iron (on the order of $10^{30}$) and a relatively low binding constant for 2-valence cations, such as calcium and magnesium. A variety of trihydroxamic acids of natural origin have been described, including compounds in the ferrichrome class, such as ferrichrome, ferrichrome A, and albomycin; compounds in the ferrioxamine class, including the ferrioxamines and ferrimycines; and compounds in the fusaramine class. The structure and iron coordination properties of these compounds have been reviewed.

One preferred chelator is ferrioxamine B, also known variously as ferrioxamine, deferoxamine, desferrioxamine B, and desferal. This compound shows exceptional iron binding affinity and has been proven safe for parenteral use in humans in treating iron-storage disease and iron-poisoning.

B. Thin-Film Hydration Method

As indicated above, the DXR/liposome dispersion may be prepared by a variety of known methods for preparing liposomes, (see, for example, Szoka 1980). One preferred method which leads to relatively high inital DXR entrapment in liposomes (up to about 95%) is the thin-film hydration approach illustrated in Example 1. In this method, vesicle-forming lipids are taken up in a suitable organic solvent or solvent system, and dried in vacuo or under an inert gas to a lipid film, which may also include a lipophilic free-radical quencher. A preferred composition (from Example 1) is egg PC:egg PG:cholesterol:alpha tocopheryl succinate (7:3:4:0.2). The lipid film is hydrated with an aqueous suspension of DXR at a final drug-to-phospholipid mole ratio of between about 1:50 to about 1:10. This produces vesicles having a DXR concentration, after removal of free DXR, of between about 2–10 mole percent. A preferred DXR:lipid mole ratio is about 1:15.

The aqueous medium used in hydrating the dried lipid film is a pyrogen free aqueous medium which contains between about 1% to 10% cryoprotectant, such as lactose or trehalose. The medium preferably contains physiological salt, such as NaCl, sufficient to produce a near-physiologic osmolarity (about 300 mOs), and DXR. A water-soluble iron chelator may also be present. A preferred medium, used in Example 1 contains 5% lactose, 0.45% NaCl, 50aem desferal, pH 5–6, and 10 mole percent (percent of lipid) DXR. The aqueous medium is added to the film, and the lipids are allowed to hydrate under rapid (with shaking) or slow (without shaking) conditions. The lipids hydrate to form a suspension of multilamellar vesicles (MLVs) whose sizes range typically between about 0.05 microns to 10 microns or greater. In general, the size distribution of MLVs in the above procedure can be shifted toward smaller sizes by hydrating the lipid film more rapidly, with shaking. The liposomes contain encapsulated chelating agent, at a concentration approximately equal to the bulk aqueous phase concentration. Typically, the concentration of liposomes in the dispersion is about 70 mM lipids.

The liposome dispersion is sized to achieve a selective size distribution of vesicles in a size range preferably between about 0.1 and 0.5 microns, as indicated above. The sizing serves to eliminate larger liposomes and to produce a defined size range having optimal pharmacokinetic properties. One preferred method for achieving the desired size distribution of liposome sizes is by extrusion of liposomes through a small-pore polycarbonate membrane sizes whose selected pore sizes, such as 0.1, 0.2, or 0.4 microns, correspond approximately to the size distribution of liposomes after one or more passes through the membrane. Typically the liposomes are extruded through the membrane several times until the size distribution stabilizes. This method of sizing is described generally by Szoka et al, 1978.

Alternatively, the liposomes can be extruded through a ceramic filter having pore sizes between about 0.2 and 1.0 microns, as described in co-owned patent application for "Liposome Extrusion Method", Ser. No. 829,710, filed Feb. 28, 1986 now U.S. Pat. No. 4,737,323).

Following liposome sizing, the dispersion is further treated to remove free DXR, i.e., DXR which is not intimately associated with the liposomes. The objective of the drug removal is to reduce the amount of free drug to a level of less than about 10% of the total DXR in the dispersion, and preferably between about 3% and 7%. The suspension can be pelleted by high-speed centrifugation after dilution, leaving free drug and very small liposomes in the supernatant. An advantage of this method is that it combines free drug removal with a concentrating step which is also useful in preparing the final dispersion. Another method uses gel filtration by molecular sieve chromatography to separate liposomes from free DXR molecules. Alternatively, the dispersion may be placed in contact with a dialysis or diafiltration-/ultrafiltration membrane whose pore size is dimensioned to selectively retain liposomes, but pass free drug. The free-drug side of the membrane may contain ion-exchange or hydrophobic groups which actively bind free DXR, to promote separation of free drug from the liposomes. The diafiltration/ultrafiltration approach has the same advantage as ultracentrifugation, in that the dispersion can be concentrated at the same time.

Another approach, described in U.S. Pat. No. 4,460,577, involves filtering a drug/liposome composition through an ion-exchange or hydrophobic resin bed to remove free drug, such as DXR. Alternatively, the material may be passed through a solid-support cartridge having with surface bound ion-exchange or hydrophobic groups capable of selectively binding DXR when the dispersion is passed through the cartridge. Such cartridges are available from Romicon (Woburn, MA).

In one preferred method for removing free drug, the dispersion is passed through a diafiltration apparatus designed to actively remove DXR that passes through the diafiltration membrane. This may be done by placing an ion-exchange or hydrophobic resin material on the filtrate side of the diafiltration membrane, or attaching ion-exchange or hydrophobic groups to support structure on this side of the membrane. The material is circulated through the membrane chamber until a final concentration of greater than about 100 mM lipid is achieved.

In the final preparation step, the dispersion is preferably concentrated to a final lipid concentration of at least about 100 mM. The purpose of concentrating the dispersion, briefly, is that following lyophilization and storage, the lyophilized material is reconstituted initially to a concentration which is also at least about 100 mM. At the same time, the reconstituted concentrate should also have a final osmolarity near physiological osmolarity, and in particular this condition should apply to intra- and extra-liposomal aqueous phase. This condition can best be met by (a) preparing the dispersion at a physiological osmolarity, and at a final concentration of greater than about 100 mM, lyophilizing the concentrated dispersion, and reconstituting the dispersion to roughly the same volume with distilled water.

As indicated above, several methods for removing free drug, such as centrifugation, diafiltration/ultrafiltration, and diafiltration/ultrafiltration in the presence of drug-binding resins, also serve to concentrate the dispersion, and the methods can readily be practiced to achieve the desired lipid concentration of at least about 100 mM. Where other free-drug removal steps are employed, the dispersion is concentrated conventionally, i.e., by ultrafiltration or centrifugation.

The final DXR/dispersion has the following characteristics:
 a. liposome sizes predominantly in a selected size range between about 0.1 to 0.5 microns, and
 b. liposome-entrapped DXR, at a concentration between about 2–10 mole percent liposome lipids, and at least about 90% liposome-associated DXR; and
 c. between about 1 and 10% cryoprotectant.

Preferably, the dispersion also has a lipid concentration of at least 100 mM, and near physiological osmolarity.

The dispersion may be sterilized by filtration through a conventional 0.22 or 0.45 micron depth filter, and lyophilized for storage.

C. Solvent Injection Method

The solvent injection method used here is based on a novel liposome preparation method described in co-owned U.S. patent applications for "High-Encapsulation Liposome Processing Method, Ser. No. 908,765 now U.S. Pat. No. 4,752,425; and "High-Concentration Liposome Processing Method:, Ser. No. 909,122, now U.S. Pat. No. 4,781,871. Both applications were filed Sept. 18, 1986. These methods are based on the discovery that, with selected solvent injection conditions, liposomes having final concentrations of up to 300–500 umole/ml, and drug entrapment efficiencies of up to 60–70% for water-soluble compounds and up to 90% or greater for lipophilic compounds can be produced in a simple batch procedure. Further, the system can be easily adapted for sizing and/or free drug removal, yielding a final product having a desired concentration, liposome size distribution, and percentage of free drug.

In preparing the DXR/liposome dispersion by solvent injection, a solution of liposome lipids in a selected solvent system is injected, at a selected rate, into a mixing chamber containing an aqueous medium with DXR, cryoprotectant, salt, buffer, and iron chelator. The lipid solvent preferably has a boiling point between about 0°–10° C, and the aqueous medium is preferably maintained between about 10°–25° C. The chamber is maintained at a constant temperature and pressure during solvent injection. The aqueous and lipid components are stirred during the infusion process by a motor-driven blade.

The liposome dispersion being formed in the mixing chamber may be sized by circulation through a sizing device designed to size the liposomes by extrusion. The device may contain a polycarbonate membrane or ceramic filter for producing extrusion and sizing. The circulation shunt containing the extrusion device may also include a dialysis or ultrafiltration unit for removing free DXR from the liposomal dispersion. The unit is constructed to allow flow-through of the liposomal dispersion, with diffusion of free DXR through a size-selective dialysis or diafiltration membrane and entrapment by ion-exchange or hydrophobic groups on the outer side of the membrane.

In operation, the lip/solvent solution is injected into the mixing chamber, with vigorous stirring, until the desired lipid concentration greater than about 100 mM is reached. AT this point, the dispersion is recirculated through the sizing/drug removal shunt until the desired size range and free drug concentration is reached.

The liposome preparation can be carried out under sterile conditions, or the dispersion can be filter sterilized as above following the solvent-injection process. The dispersion is then lyophilized for storage.

II. Liposome Reconstitution

To prepare the lyophilized DXR/liposome composition for injection, in dilute form, the composition is first reconstituted to form a liposome concentrate. The concentrate is then diluted with an injection medium, such as physiological saline, to form a dilute DXR/liposome suspension suitable for parenteral injection. The reconstitution/dilution steps used in preparing lyophilized composition for injection are important in minimizing he amount of free drug in the diluted suspension, as will be seen below, and form an important part of the present invention. This section examines the behavior of the lyophilized DXR/liposomes in the reconstitution step.

A. Size Characteristics

In order to control liposome sizes in the reconstituted DXR/liposome material, it is necessary to minimize liposome size changes on lyophilization and reconstitution. Experiments conducted in support of the present invention indicate that sized liposomes, in the absence of cryoprotectants, increase substantially in size in a lyophilization/reconstitution cycle.

This can be seen from the study reported in Example 3, which examined size changes in a liposome concentrate containing either 125 mM trehalose (about 5%), 5% lactose, or 5% mannitol. Original liposome sizes, produced by extrusion through a 0.2 micron polycarbonate filter, averaged between about 280 to 335 nm, as seen in Table 1. Each of the three dispersion was frozen slowly in controlled freezer chamber, or quick frozen in liquid nitrogen, then lyophilized to complete dryness. The preparations were then reconstituted with distilled water to the original dispersion volume, and analyzed for liposome size distribution. Average sizes are shown in the lower rows in Table 1. As seen, both trehalose and lactose, but no mannitol, were effective in preventing liposome size changes on lyophilization/reconstitution. The increase in liposome sizes observed in the mannitol formulation was comparable to that seen in the absence of a cryoprotectant sugar.

B. Lipid Concentration

According to an important aspect of the invention, it has been discovered that the extent of release of liposome-bound DXR from lyophilized DXR/liposomes can be reduced significantly by initial reconstitution to a relatively high lipid concentration, at least about 100 umole lipid/ml, then further dilution with a isotonic injection medium. The effect of lipid concentration on DXR drug release on reconstitution can be seen from the study reported in Example 4. Briefly, four DXR/liposome dispersions prepared as above, and concentrated to increasing lipid concentrations between 40 and 211 mM, were initially examined for percent free DXR. This was done, as detailed in Example 4, by molecular sieve chromatography in a salt solution which is iso-osmotic with the liposome formulation. As shown in Table 2, the formulations had between 11% and 13% free DXR.

After lyophilization, the dried composition were reconstituted with either 250 ul (one-half original volume) or 500 ul (original volume) of distilled water, and the reconstituted formulations were again analyzed for percent free DXR, with the results shown in the lower two rows in Table 2. As seen, diluting the lyophilized material to 40 or 54 mM (third row, first two columns) produced an increase of 7–8% in the amount of free DXR, whereas at the higher concentrations, (80 to 422 mM), at most an increase of 4% in free DXR was observed.

Similar results were obtained in the second study reported in Example 4. Here DXR/liposome dispersions having the lipid concentrations shown in Table 2, and free drug concentrations before lyophilization of about 6%, were lyophilized and reconstituted with distilled water to an original volume. The column at the right in the table shows the measured percentages of free drug after reconstitution. As above, at reconstitution lipid concentrations below about 100 mM, final free drug concentrations increased about 8–9%. At higher concentrations, the increase was about 3–4%.

After reconstitution to form a liposome concentrate, additional dilution with isotonic medium appears to have little or no effect on the percent free drug in the suspension. It is also noted here that all of the percentage of free or bound drug reported above were determined by molecular sieve chromatography, which itself produces a several fold dilution of the DXR/liposome concentrate or suspension being tested.

However, further dilution of the concentrate can lead to release of DXR from the liposomes if the diluting medium is hypotonic. This is true even at high lipid concentration, as demonstrated by the study in Example 4. Here a DXR/liposome dispersion containing 138 mM lipid in 5% lactose and 0.45% saline was lyophilized in 0.5 ml aliquots, then reconstituted with increasing amounts of distilled water, from 50 to 500 ul. Following reconstitution, and after standing at room temperature for 1 hour, the concentrate was diluted with distilled water to approximately the original concentration (138 mM). Thus, for example, the first sample shown in Table 4 was reconstituted with 50 ul (10X original concentration), then further diluted with 450 ul of distilled water to about 1 X concentrate, whereas the final sample shown in the table was reconstituted directly with 500 ul of distilled water to the lX concentration end point. Table 4 gives the percent DXR associated with the resulting DXR/liposomes, as measured by molecular sieve chromatography, for each of two identically treated samples. As seen, dilution conditions which produce greater hypertonic liposome swelling also produce greater loss of liposome-bound DXR.

Since reconstituting or DXR/liposomes under conditions which cause liposome swelling significantly increase the amount of free drug release, it was also of interest to determine if hypotonic swelling on reconstitution increased free DXR release. Here DXR/liposomes prepared in an isotonic dispersion (about 300 mOs) were lyophilized and reconstituted to a final lipid concentration of about 150 mM with either distilled water or 0.9% NaCl. Presumably, in the case of reconstitution with distilled water, the bulk phase medium was isotonic with the liposome interior spaces, whereas in the case of reconstitution with isotonic saline, the outer bulk phase has roughly twice the osmolarity of the liposome interior spaces, causing some liposome shrinkage. The percent of free drug in the pre-lyophilized dispersion is about 4%. With both reconstitution media, the percentage of free DXR after reconstitution is between about 6–7%. The results indicate that at least mild shrinkage on reconstitution can be tolerated without increased release of free DXR into the reconstitution medium.

Three significant features of the above data stand out. First, reconstitution of lyophilized liposomes necessarily causes some loss of liposome-bound DXR. (Here it is noted that the liposome concentrates show no increase in free DXR when stored at 4° C for several months, indicating that the DXR leakage observed on lyophilization is related to the lyophilization process). This indicates that reconstituting the liposomes involves some brief period of membrane alteration in which DXR can be released from liposomes. This loss can be minimized, according to one aspect of the invention, by reconstituting the liposomes to a relatively concentrated solution. One possible explanation for this phenomenon is that during the brief period when drug is released from the membrane, it partitions rapidly between lipid and bulk aqueous phases in the reconstitution medium in proportion to the relative concentrations of lipid and bulk aqueous phases in the medium. A higher lipid concentration would thus favor greater partitioning in the liposomes during reconstitution. Alternatively, the extent of membrane alteration and drug release during reconstitution may is less at a higher liposome concentration.

Secondly, a DXR/liposome concentrate can be diluted with an isotonic dilution medium without appreciable release of free drug, even after extended storage periods. This behavior indicates that DXR binding to liposomes is not controlled by a dynamic equilibrium exchange, which would be concentration dependent. Rather it appears that DXR release from (and perhaps binding to) liposomes only occurs during periods of membrane perturbation, such as during reconstitution or under conditions of osmotic swelling. This feature allows the liposome concentrate, which itself has a minimum free drug content, to be diluted for injection without appreciable increase in the percentage of free drug.

Thirdly, liposome swelling causes a significant increase in free DXR release from reconstituted membranes, although mild shrinkage on reconstitution appears to have no effect on free drug release. This feature places certain limitations on the nature of the dilution media which are appropriate for use in the method of the invention. Typically, the final dilution medium is physiological saline, in which case the liposome concentrate should not be more than about 2X physiological saline, to avoid substantial liposome swelling. Preferably hypotonic shrinkage is also avoided by reconstituting the lyophilized liposomes to a final osmolarity not less than about 0.5 physiological osmolarity (about 300 mOs). In a preferred embodiment of the invention, the liposome dispersion is prepared at physiological osmolarity, reconstituted to the original concentrate volume with distilled water, and diluted with physiological saline. The final concentration of the diluted injectable suspension is one suitable for IV injection, such as between about 2 to 20 mM lipid.

C. Temperature Conditions

The effect of storage temperature and material temperature on reconstitution on free drug release have also been examined, with the results seen in Example 6. Briefly, lyophilized DXR/liposomes were stored at either − 20° C or 4° C for several days, and the samples were reconstituted to the original volume with room temperature distilled water either at the storage temperature, or after equilibrating the lyophilized material to room temperature. In all cases, the percentage of liposome-bound DXR was between about 90% to 92%, as seen from the data in Table 5. Thus storage temperature or the temperature of the lyophilized material has little or no effect on the extent of release of free drug from the liposomes on reconstitution.

III. DXR/Liposome Administration

This section examines the preparation and use of the DXR/liposome formulation of the invention in a clinical setting, including preparations and storage considerations, and utility in tumor treatment.

A. Preparation and Storage

The DXR/liposome formulation is supplied as a lyophilized composition. As discussed in Section II, the composition, when reconstituted with a predetermined amount of aqueous medium, is characterized by:
 a. a concentration of liposomes of greater than about 100 mM liposome lipid,
 b. liposome sizes predominantly in a selected size range between about 0.1 to 0.5 microns,
 c. liposome-entrapped DXR, at a concentration between about 2–10 mole percent liposome lipids, and between about 85–95% liposome-associated DXR; and
 d. between about 1% and 10% cryoprotectant.

Preferably, the composition is reconstituted with distilled water to an original volume of liposome dispersion.

An advantage of the lyophilized composition is that it can be stored long term at refrigerator or room temperature without appreciable lipid oxidative or hydrolytic degradation. At the same time, the material can be reconstituted to a concentrate having desired selected liposome size distribution in the 0.1 to 0.5 micron size range, and with only slight loss of DXR into the bulk phase medium.

For convenience of preparation and also to minimize drug losses, it is desirable to supply the lyophilized material in a multi-dose quantity which, when reconstituted, provides several aliquots for dilution and individual-dose drug administration. As an example, the lyophilized material may be supplied in a quantity containing 1 g (about 1.84 mmoles) of DXR in a total of about 20 mmoles lipid. The lyophilized material is then reconstituted with about 100 ml distilled water to a final concentration of about 200 mM lipid. The liposome concentrate may be stored at 4 C for several weeks without significant degradation, if protected by alpha-tocopherol and desferal, as discussed. The single diluted dose can be prepared easily from the above concentrate, by simple dilution with sterile saline. For example, to administer a 50 mg dose, a 5 ml aliquot of the concentrate is withdrawn and added to about 120 ml of sterile saline, and this suspension is then delivered conventionally by iv drip or the like. Alternatively, for syringe injection, the concentrate may be diluted to a smaller volume, preferably 25 to 50 ml, for administration. Thus the concentrate can be used to prepare between about 10-40 individual doses.

Alternatively, the lyophilized material may be supplied in individual dose form, such as in a multicompartment package containing, in individual sealed compartments, (a) the desired amount of lyophilized DXR/liposome composition, (b) a quantity of reconstitution medium sufficient to form the DXR/liposome concentrate, when mixed with the lyophilized composition, and (c) the dilution medium. The concentrate is initially formed by allowing mixing of the (a) and (b) compartments, and the final diluted medium, by allowing mixing between the concentrate and compartment (c).

B. Therapeutic Uses in Tumor Treatment

Earlier studies described in the above-cited patent application for "Liposome/Anthaquinone Drug Composition and Method" have shown that small, drug-carrying liposomes can concentrate liposome-associated drug in tissue regions, such as liver sinusoids and parenchyma, spleen, and bone marrow which are accessible to relatively small liposomes. These findings having important implications for treating metastatic diseases of the liver, primary hepatomas, lymphoid proliferative diseases, and leukemias, all of which are major cancers, both in terms of numbers and geographic distribution.

Clinical trials using DXR/liposomes to treat metastatic tumors of the liver have been undertaken. The treatment results obtained to date indicate a significant improvement in overall patient comfort with liposome entrapped DXR, due to virtually complete elimination of gastrointestinal toxicity (nausea, vomiting, diarrhea, and stomatitis), and no pain at the site of injection. The results represent a major improvement in treatment of certain cancers with DXR. In addition, there is a significant reduction in alopecia in the treated patient, and therapeutic effectiveness appears to be as good or better than free DXR alone, as evidenced by changes in tumor size. The clinical trials with DXR/liposome suspensions containing different percentages of free DXR indicate that significantly greater reduction in side effects is seen as the percentage of free DXR in the suspension is reduced.

From the foregoing, it can be appreciated how various objects and features of the invention are met. The lyophilized composition of the invention provides a convenient and stable form of DXR/liposomes that can be stored for extended periods (up to several months or more) at refrigerator or room temperature without degradation of either lipid or drug components.

The lyophilized composition is readily reconstituted to a concentrate having a desired liposome size distribution and at least about 85%, and more typically, 90-95% liposome-associated DXR. The concentrate in turn can be diluted for parenteral administration without significantly changing liposome size or percentage of liposome-bound drug. The diluted medium has advantageous biodistribution properties, due to the size distribution of liposomes, and low toxicity, due both to the integrity of the liposome and DXR components, and to the low percentage of free DXR.

The following examples illustrate methods of preparation and properties of the DXR/liposome concentrates and suspensions formed according to the invention. The examples are in no way intended to limit the scope of the invention.

Materials

Doxorubicin HCl (DXR) was obtained from Laboratoire Roger Bellon, SA; EPC and EPG, from Avanti Polar Lipids, Inc., (Birmingham, AL); cholesterol, alpha-tocopheryl succinate, lactose, and mannitol, from Sigma Chemical (St. Louis, MO); desferal, from CIBA (Summit, NJ); and trehalose dihydrate, from, Pfanstiehl Laboratories Inc. (Waukegan, IL).

EXAMPLE 1

Preparation of Lyophilized DXR/Liposomes

A chloroform solution of lipids containing 518.6 mg EPC, 210.4 mg EPG, 140.0 mg cholesterol and 9.8 mg of alpha-tocopherol succinate was prepared. The solvent was removed by rotary evaporation under reduced pressure followed by exposure of the sample to a vacuum of less than 50 microns Hg for 2h to eliminate solvent residuals. 20 ml of an aqueous solution containing 2.67 mg/ml DXR, 5% lactose, 0.45% NaCl and 50 uM desferal was added to the dried lipid (molar ratio of PC:PG:cholesterol:alpha-tocopheryl tocopheryl succinate:DXR 7:3:4:0.2:1). Approximately 20 glass beads of 6 mm diameter were also added to facilitate the lipid hydration process. The mixture was then shaken on a wrist shaker for 2-3 h at r.t. The MLVs thus formed were extruded through a 0.2 u polycarbonate membrane five times in a 50 ml Amicon ultra-filtration cell under pressure. The DXR/liposomes had the following characteristics at this stage of the preparation process:
 (a) total DXR incorporated into liposomes was 85-90% of the initial amount of drug added (determined by Sephadex gel permeation chromatography);
 (b) total lipid concentration was 55-68 umole/ml (determined by organic phosphate present);
 (c) the mean particle size of the preparation was 300-400 nm in diameter (determined by Dynamic Laser light scattering technique);
 (d) 80% of the total DXR was still liposome associated after incubation of the preparation with 50% human plasma for 1h at 37° at a final liposome concentration of 2.5 umole/ml.

The DXR/liposome dispersion was treated with Dowex ion exchange resin (19 mg Dowex 50 x:4-400 resin used/mg DXN) for 10 minutes at r.t., resulting in less than about 5% free DXR. After removing the resin materials, the liposome concentration was brought up to approximately 150 umole/ml by a centrifugation sedimentation procedure.

500 ul samples of this concentrated liposome preparation were aliquoted into individual vials and placed in the lyophilizer with its shelf temperature set at 5° C (Virtis Lyophilizer). When the sample temperature equilibrated to 5° C, the shelf temperature was reduced to −5° C. The vacuum was activated when the temperature of the samples reached −30° to −35° C. The samples were lyophilized at −35° C for 48h at a vacuum of less than 5 um of Hg, at which time the shelf temperature was raised to − 25° C for 4 h. Samples were then sealed under vacuum and stored at 4° C until used.

EXAMPLE 2

Size Characteristics of Reconstituted DXR/Liposomes

Liposomes were prepared in 125 mM trehalose-0.45% NaCl, 5% lactose-0.45% NaCl or 5% mannitol containing DXR in 10 mM Tris-HCl at pH 7.4 using the procedure described in Example 1, except that glass beads were not added to the lipid hydration mixture. After the polycarbonate membrane extrusion step, 6 ml of each of the three preparations were diluted six fold in 10 mM Tris-HCl-0.0% NaCl and pellets at approximately 150,000 X g for 30 minutes. The pellets were then suspended in pb 10 ml of buffer containing the appropriate cryoprotectant. Approximately 30% of the total DXR was not liposome associated at this point. 500 ul samples were frozen either by exposing them to liquid nitrogen or by placing them in a controlled freezing chamber (Cryomed). Subsequent lyophilization and reconstitution steps were carried out as described in Example 1. For particle size measurements, pre or post-lyophilization (reconstituted) samples were diluted 200 fold in appropriate sugar solutions and measurements were made in a dynamic laser light scattering instrument (Nicomp Model 200, Maryland). As seen from the particle size data given in Table 1 below, both trehalose and lactose effectively prevented liposome size growth on lyophilization and reconstitution.

TABLE 1

| | Particle Size (nm) | | |
|---|---|---|---|
| | 125 mM trehalose | 5% lactose | 5% mannitol |
| Original Sample | 284 | 303 | 335 |
| Slow Freeze | 247 | 266 | 779 |

TABLE 1-continued

| | Particle Size (nm) | | |
|---|---|---|---|
| | 125 mM trehalose | 5% lactose | 5% mannitol |
| Rapid Freeze | 257 | 269 | 696 |

EXAMPLE 4

Effect of Lip Concentration

Liposomes were prepared as described in Example 1 except the liposomes were not treated with Dowex resin. After polycarbonate membrane extrusion, aliquots of the preparations were diluted tenfold with 0.9% NaCl-50uM desferal and liposomes were pelleted at 150,000 X g for 1h. The liposome pellets were then resuspended in 5% lactose-0.45% NaCl-50 uM desferal to different lipid concentrations (40, 54, 143, 211 mM). These preparations contained 11–13% free DXR at this point. 500 ul aliquots of each of these samples were lyophilized as described in Example 1. The lyophilized materials were reconstituted by adding either 250 ul or 500 ul of distilled water. The percent free DXN was determined by running the sample on a Sephadex G-50 column and analyzing the amount of DXN in the liposome peak eluted in the void volume of the column versus that eluted as free DXN in the bed volume of the column. Samples that were reconstituted with 500 ul of distilled water were analyzed on a column equilibrated in 0.9% saline-50 uM desferal while those reconstituted with 250 ul water were analyzed in a column equilibrated in 1.8% saline-50 uM desferal. The percentage of free DXR in the analyzed samples is shown in Table 2. The results are discussed in the text above.

TABLE 2

| | % Free DXN | | | |
|---|---|---|---|---|
| | 40 mM | 54 mM | 143 mM | 211 mM |
| Original Sample | 13% | 12% | 13% | 11% |
| 250 lambda H2O | 16% | 13% | 12% | 15% |
| 500 lambda H2O | 22% | 20% | 16% | 16% |

In a second study, DXR/liposomes were prepared and lyophilized as described in Table 2, with the exception that the liposomes were treated with Dowex resin as described in Example 1 to bring the free DXR level to 5–6% prior to liposome concentration by centrifugation pelleting. Lyophilized materials were reconstituted in 500 ul distilled water and the percent free DXN was determined using a standard Sephadex G-25 centrifugation technique. The percent of liposome-bound drug is shown in Table 3.

TABLE 3

| Lipid Concentration (umole/ml) | % DNX Incorporation (reconstituted) |
|---|---|
| 52 | 85% |
| 60 | 86% |
| 106 | 91% |
| 154 | 91% |
| 181 | 90% |
| 215 | 91% |

EXAMPLE 4

Rehydration Conditions

Liposomes were prepared and lyophilized as described in Example 1. Pre-lyophilized sample had 4% free DXN and a lipid concentration of 200 umole/ml. The lyophilized materials were reconstituted by adding an initial amount of distilled water (50, 100, 250 or 500 ul), letting the samples sit at r.t. for 1h, and adding additional water to bring the total volume of added water to 500 ul. Percent liposome-bound DXR was determined as above, with the results shown in Table 4. The data, discussed above, shows increasing release of DXR into the medium with greater hypertonic liposome swelling.

TABLE 4

| Rehydration Conditions Incorporation | % DXN |
|---|---|
| 50 ul H2O, 1h (rt) + 450 ul H2O | 77% |
| | 84% |
| 100 ul H2O, 1h (rt) + 400 ul H2O | 85% |
| | 82% |
| 250 ul H2O, 1h (rt) + 250 ul H2O | 88% |
| | 84% |
| 500 ul H2O | 91% |
| | 89% |
| 500 ul H2O (138 mM lipid) | 89% |

EXAMPLE 5

Reconstitution Temperature Conditions

Liposomes were prepared and lyophilized as described in Example 1. Pre-lyophilized sample contained 6% free DXR and had a lipid concentration of 110 umole/ml. The lyophilized materials were stored at 4% or −20° for 2 weeks and reconstituted with 500 ul water according to the procedures described in Table 5. Percent DXR was analyzed by the above Sephadex G-25 centrifugation technique. As seen from the DXR Liposome-association data shown in Table 5, the release of free drug from liposomes was substantially independent of storage and reconstitution temperature.

TABLE 5

| Reconstitution Conditions | % DXN Incorporation |
|---|---|
| Stored at −20° C., add H2O (rt) | 90% |
| Stored at −20° C., equilibrate sample to rt (2h), add H2O at rt | 91% |
| Stored at 4° C., add H2O at rt | 92% |
| Stored at 4° C., equilibrate sample to rt (2h), add H2O at rt | 90% |

EXAMPLE 6

Storage Stability of Reconstituted DXR/Liposomes

Liposomes were prepared and lyophilized as described in Example 5. Lyophilized samples were reconstituted immediately after lyophilization. Reconstituted samples were stored at 4° and percent free DXR was determined using the Sephadex G-25 centrifugation technique at different time point of storage, as indicated at the left in Table 6 below. The table also gives the percentage of liposome-bound DXR measured after the designated storage period.

TABLE 6

| Time After Reconstitution (days) | % DXN Incorporation |
|---|---|
| 0 | 84% |
| 14 | 88% |
| 30 | 89% |
| 60 | 90% |

Although the invention has been described with respect to particular formulations, preparation conditions, and uses, it will be appreciated that various modifications or changes may be made without departing from the invention.

It is claimed:

1. A method of preparing an injectable doxorubicin/liposome suspension containing at least about 85% liposome-entrapped doxorubicin, comprising
    reconstituting a dehydrated liposome composition characterized, in a pre-dehydration liposome dispersion, by:
    a. liposome sizes predominantly in a selected size range between about 0.1 to 0.5 microns,
    b. liposome-entrapped doxorubicin, in an amount which is at least about 90% of the total doxorubicin, and
    c. between about 1% to 10% cryoprotectant, with an aqueous medium to a final liposome concentration of greater than about 100 mM lipid,
    by said reconstituting, forming a liposome concentrate which shows substantially no increase in free doxorubicin when stored at 4° C for up to several months, and
    diluting the reconstituted concentrate with an aqueous medium to a final liposome concentration suitable for intravenous injection.

2. The method of claim 1, wherein the liposome concentrate further includes liposome-entrapped alpha-tocopherol or a pharmacologically acceptable analog, derivative, or ester thereof.

3. The method of claim 1, wherein the liposome concentrate further includes a trihydroxamic chelating agent in molar excess of the ferric iron in the suspension.

4. The composition of claim 1, wherein the liposomes includes between about 30–70 mole percent phosphatidyl choline, 20–50 mole percent cholesterol, and between about 10–50 mole percent of a negatively charged phospholipid or sterol.

5. The method of claim 1, wherein the liposome dispersion has a lipid concentration of at least about 100 mM, and an osmolarity near physiological osmolarity, and the aqueous medium used for said reconstituting includes distilled water or dilute saline in an amount which produces a lipid concentration in the reconstituted composition approximates the lipid concentration of the lipid dispersion, and the aqueous medium used for diluting the reconstituted composition is a physiological salt solution, in an amount which produces a final lipid concentration suitable for intravenous injection.

6. The method of claim 1, wherein the pre-dehydration liposome dispersion contains between about 5%–10% cryoprotectant.

* * * * *

UNITED STATES PATENT AND TRADEMARK OFFICE
CERTIFICATE OF CORRECTION

PATENT NO. : 4,927,571                                Page 1 of 2

DATED      : May 22, 1990

INVENTOR(S) : A. Huang, S. Krishnan

It is certified that error appears in the above-identified patent and that said Letters Patent is hereby corrected as shown below:

n the Abstract:

Last line, last word, replace "perenteral" with --parenteral;

Column 1, line 16, between the alpha letters USA and 78 delete "(";

Column 1, line 38, after the word Young replace "}" with --)--;

Column 2, line 47, replace first word "pheral" with --pherol--;

Column 4, line 23, replace last word ":;ill" with --will--;

Column 6, line 13, replace "50aem" with --50µm--;

Column 8, line 41, replace "lip" with --lipid--;

Column 8, line 44, replace "AT" with --At--;

Column 8, line 61, replace "he" with --the--;

Column 13, line 62, delete the word "tocopherol";

Column 14, line 17, delete the ":"

Column 14, line 46, replace "0.0%" with --0.9%--;

Column 15, line 8, replace "Lip" with --Lipid--;

Column 16, line 19, insert under column heading %DXN delete "89%" replace th --90%--;

UNITED STATES PATENT AND TRADEMARK OFFICE
CERTIFICATE OF CORRECTION

PATENT NO. : 4,927,571

DATED : May 22, 1990

INVENTOR(S) : A. Huang, S. Krishnan

It is certified that error appears in the above-identified patent and that said Letters Patent is hereby corrected as shown below:

Column 16, line 20, insert under column heading %DXN --89%--;

Column 16, line 60, replace "Incorporation" with --Reconstitution--;

Column 18, line 7, replace "includes" with --include--.

Signed and Sealed this

Eleventh Day of June, 1991

Attest:

HARRY F. MANBECK, JR.

Attesting Officer

Commissioner of Patents and Trademarks